(12) United States Patent
Syrjälä et al.

(10) Patent No.: US 12,213,815 B2
(45) Date of Patent: Feb. 4, 2025

(54) CT IMAGING APPARATUS

(71) Applicant: PLANMECA OY, Helsinki (FI)

(72) Inventors: Tommi Syrjälä, Helsinki (FI); Lauri Seppälä, Helsinki (FI); Timo Müller, Helsinki (FI); Kari Malmén, Helsinki (FI)

(73) Assignee: PLANMECA OY (FI)

( * ) Notice: Subject to any disclaimer, the term of this patent is extended or adjusted under 35 U.S.C. 154(b) by 410 days.

(21) Appl. No.: 17/616,026

(22) PCT Filed: Jun. 1, 2020

(86) PCT No.: PCT/FI2020/050372
§ 371 (c)(1),
(2) Date: Dec. 2, 2021

(87) PCT Pub. No.: WO2020/245500
PCT Pub. Date: Dec. 10, 2020

(65) Prior Publication Data
US 2022/0296178 A1    Sep. 22, 2022

(30) Foreign Application Priority Data

Jun. 3, 2019  (FI) ...................................... 20190042

(51) Int. Cl.
*A61B 6/03*    (2006.01)
*A61B 6/00*    (2006.01)
(Continued)

(52) U.S. Cl.
CPC .............. *A61B 6/032* (2013.01); *A61B 6/035* (2013.01); *A61B 6/0407* (2013.01); *A61B 6/08* (2013.01);
(Continued)

(58) Field of Classification Search
CPC ....... A61B 6/032; A61B 6/035; A61B 6/0407; A61B 6/08; A61B 6/40; A61B 6/4429;
(Continued)

(56) References Cited

U.S. PATENT DOCUMENTS

2003/0021386 A1    1/2003  Tanaka
2005/0058257 A1    3/2005  Fischer et al.
(Continued)

FOREIGN PATENT DOCUMENTS

WO    2018098147 A1    5/2018
WO    2019056055 A1    3/2019

OTHER PUBLICATIONS

International Search Report for PCT/FI2020/050372, Mailed Sep. 22, 2020, 4 pages.

*Primary Examiner* — David P Porta
*Assistant Examiner* — Mamadou Faye
(74) *Attorney, Agent, or Firm* — Lippes Mathias LLP

(57) ABSTRACT

The invention relates, in particular, to structures of dental and medical cone beam computed tomography (CBCT) imaging apparatus. The basic construction of the apparatus includes a substantially vertically extending frame part (11) which supports via a horizontally extending support construction (12) the X-ray imaging means (14, 15) of the apparatus. The apparatus includes a patient support structure (18) which extends substantially in parallel with and is essentially of the same length as the substantially vertically extending frame part (11).

20 Claims, 7 Drawing Sheets

(51) Int. Cl.
*A61B 6/04* (2006.01)
*A61B 6/08* (2006.01)
*A61B 6/40* (2024.01)
*A61B 6/51* (2024.01)
*A61B 6/58* (2024.01)
*A61B 5/00* (2006.01)

(52) U.S. Cl.
CPC .............. *A61B 6/40* (2013.01); *A61B 6/4429* (2013.01); *A61B 6/4435* (2013.01); *A61B 6/4452* (2013.01); *A61B 6/4476* (2013.01); *A61B 6/51* (2024.01); *A61B 6/54* (2013.01); *A61B 6/587* (2013.01); *A61B 5/0088* (2013.01)

(58) Field of Classification Search
CPC ... A61B 6/4435; A61B 6/4452; A61B 6/4476; A61B 6/51; A61B 6/54; A61B 6/587; A61B 5/0088; A61B 6/0442; A61B 6/0487; A61B 6/4085; A61B 6/4447; A61B 6/501; A61B 6/04; A61B 6/4458; A61G 2210/50; A61G 7/005; A61G 13/04; A61G 13/02; A61G 15/02
See application file for complete search history.

(56) References Cited

U.S. PATENT DOCUMENTS

2012/0324648 A1   12/2012  Amano
2020/0268332 A1*  8/2020  Gregerson ........... A61B 6/4476

* cited by examiner

CT IMAGING APPARATUS

FIELD OF THE INVENTION

The invention relates to computed tomography imaging apparatus. In particular, features of an apparatus according to the invention are applicable for use in the context of dental and medical cone beam computed tomography (CBCT) imaging apparatus.

BACKGROUND OF THE INVENTION

Computed tomography (CT) is a kind of X-ray imaging in which a volume to be imaged is irradiated from different directions and, from the image information thus acquired, a desired two- or three-dimensional image can be reconstructed.

Traditional CT apparatus are large and massive, and they are typically mounted on a floor. A patient is positioned for imaging within an examination opening of the apparatus, typically on a horizontally extending and laterally movable examination platform.

Since development of cone beam computed tomography (CBCT) technology in which, for one, slower rotational speeds of the imaging means are used, apparatus of less weight than that of the more traditional CT apparatus have been developed. Among the CBCT apparatus, there are also e.g. ones which are not floor mounted but constructed to be mobile. Also, constructions comprising a vertically extending frame and a horizontally extending support for the imaging means have been designed. Such support may comprise e.g. a ring-shaped gantry or a so-called C-arm and such apparatus may have been designed e.g. in view of the needs of cranial imaging. Rotating of the imaging means is known to be arranged to take place about a (virtual) vertical rotation axis and in such context, supports specifically designed to help a patient keep one's head still while standing during an exposure have been developed.

BRIEF DESCRIPTION OF THE INVENTION

The object of the invention and of its preferable embodiments is a CT apparatus, especially a CBCT apparatus, applicable for versatile use and enabling imaging various parts of an anatomy. The characteristic features of the invention are defined in claim 1

BRIEF DESCRIPTION OF THE FIGURES

The invention is now described in more detail in reference to its preferable embodiments and the attached drawings, of which.

DETAILED DESCRIPTION OF THE INVENTION

Figure 1:
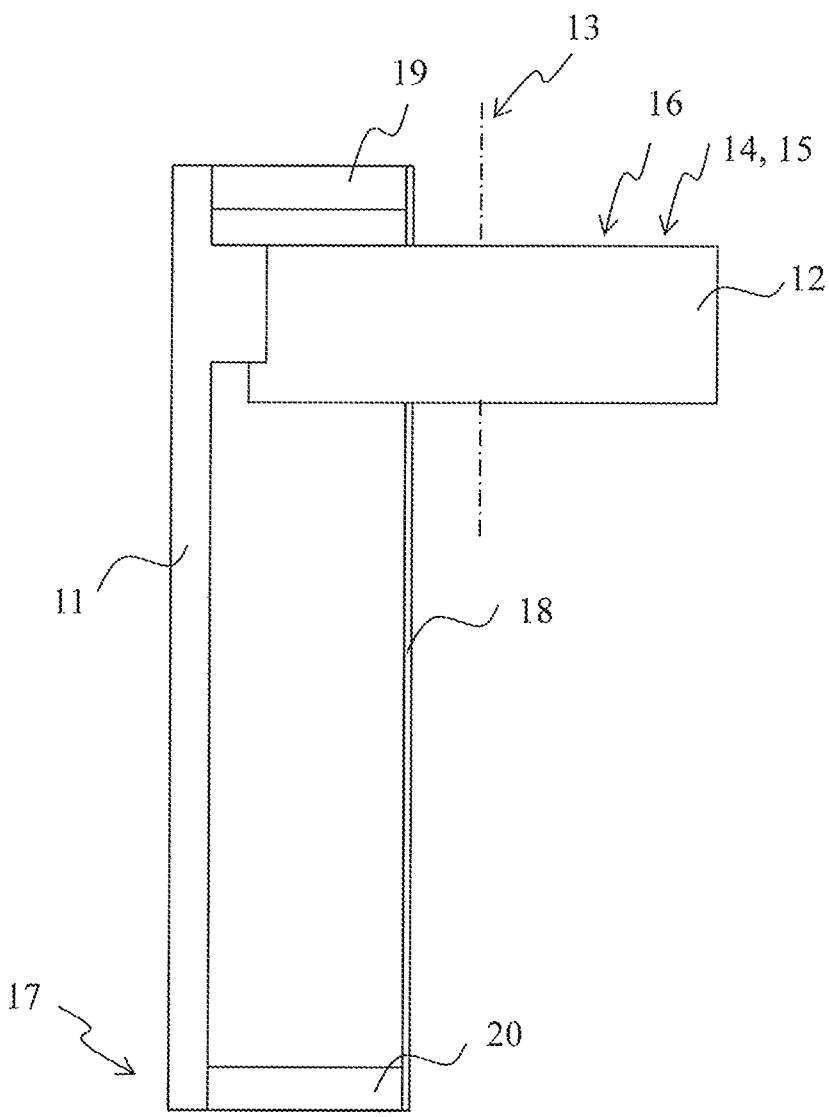
FIG. 1 is a schematic general side view showing certain components of one embodiment, as an example, of an apparatus according to the invention.

FIG. 1 shows a schematic general side view of certain components of one embodiment, as an example, of an apparatus according to the invention. The dental or medical CT imaging apparatus of FIG. 1 comprises a substantially vertically extending frame part 11 having a top end and a bottom end. From this substantially vertically extending frame part 11 extends essentially horizontally a support construction 12 which supports an X-ray source 14 and an image detector 15 yet which as such are not visible in FIG. 1. The X-ray source 14 and the image detector 15, which together form X-ray imaging means 14, 15, may be mounted to the support construction 12 essentially opposite to each other yet in embodiments, their mutual position may also be arranged to be adjustable.

FIG. 1 further shows a patient support 18 which is a structure mechanically connected to the substantially vertically extending frame part 11 and extending substantially in parallel with the substantially vertically extending frame part 11. In the embodiment of FIG. 1, the patient support 18 is essentially of the same length as the substantially vertically extending frame part 11.

According to one aspect, for example, the length of the substantially vertically extending frame part 11 is of the order of 240 cm.

According one aspect, for example, the length of the substantially vertically extending frame part 11 is between 220 cm and 260 cm.

According one aspect, for example, the length of the patient support 18 is 80-90% of the length of substantially vertically extending frame part 11.

According to one aspect, for example, the patient support 18 has a longer dimension in a first direction and a shorter dimension in a second direction orthogonal to the first direction.

According to one aspect, for example, the patient support 18 is at least in the first direction at least for its prevailing part radiolucent.

According to one aspect, for example, the radiolucent part of the patient support 18 is of essentially the same length as the substantially vertically extending frame part 11.

According to one aspect, for example, the patient support 18 comprises at least at either of its ends in the first direction a section which is not radiolucent.

According one aspect, for example, the length of the radiolucent part of the patient support 18 in the first direction is 80-90% of the length of the substantially vertically extending frame part 11.

According to one aspect, for example, the support construction 12 supporting the X-ray imaging means 14, 15 is a circular gantry having a central axis 13. The gantry may partially encircle or completely house the X-ray imaging means 14, 15.

According to one aspect not directly visible in FIG. 1, for example, the apparatus comprises a driving mechanism 16 arranged to drive the X-ray imaging means 14, 15 about a rotation axis. The rotation axis may coincide with the central axis 13 of the support construction 12 in form of the gantry and it may be a physical axis, or a virtual rotation axis as in the case of FIG. 1.

According to one aspect, for example, the central axis 13 of the gantry coincides with the center of rotation/the rotation axis of the X-ray imaging means 14, 15 when they are driven along a curved path.

According to one aspect, the rotation axis is an instantaneous (virtual) rotation axis and the location of the instantaneous rotation axis in relation to the central axis 13 can be arranged to be changed.

According to one aspect, at least either of the components the ray source 14 and the image detector 15 is arranged to be laterally movable from a location exactly opposite to the other component.

According to one aspect, the structure 12 supporting the X-ray imaging means 14, 15 comprises a gantry having a central axis and the structures of apparatus allow for at least either of: laterally moving the X-ray source 14 between positions at which a central ray it generates coincides with the central axis of the gantry and a position at which the central ray it generates does not coincide with the central axis of the gantry; laterally moving the image detector 15 between positions at which a vector which is normal to the detector surface at the center of the image detector 15 coincides the central axis of the gantry and a position at which the vector which is normal to the detector surface at the center of the image detector 15 do not coincide the central axis of the gantry. The lateral moving of the X-ray imaging means 14, 15 may include moving the X-ray imaging means 14, 15 to a position at which they face each other while the central ray the X-ray source 14 generates does not coincide the central axis of the gantry and the vector which is normal to the detector surface at the center of the image detector 15 does not coincide the central axis of the gantry.

According to another aspect, another driving mechanism 17 is arranged to the apparatus to enable moving the support construction 12 back and forth in a direction which is substantially parallel with the direction in which the substantially vertically extending frame part 11 extends. According to one aspect, that driving mechanism 17 may be arranged to move the support construction 12 along or alongside the substantially vertically extending frame part 11.

Figure 2A:
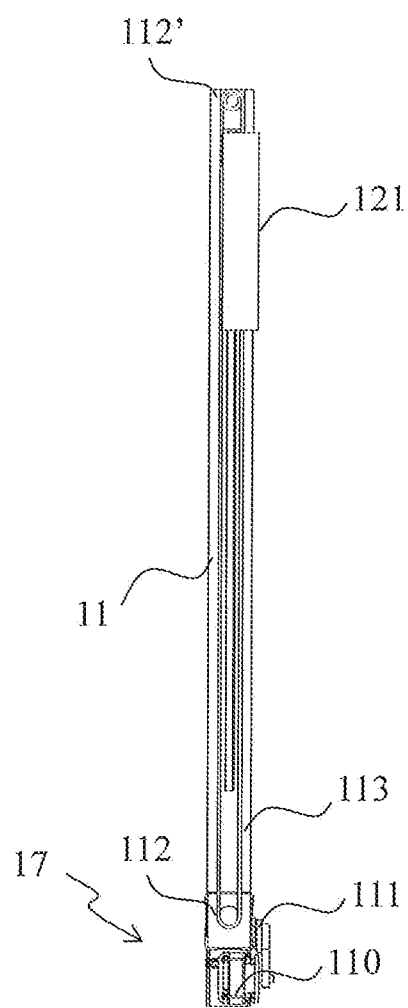
FIGS. 2a and 2b show structural details applicable for use in the context of the vertically extending frame of the apparatus of FIG. 1.
Figure 2B:
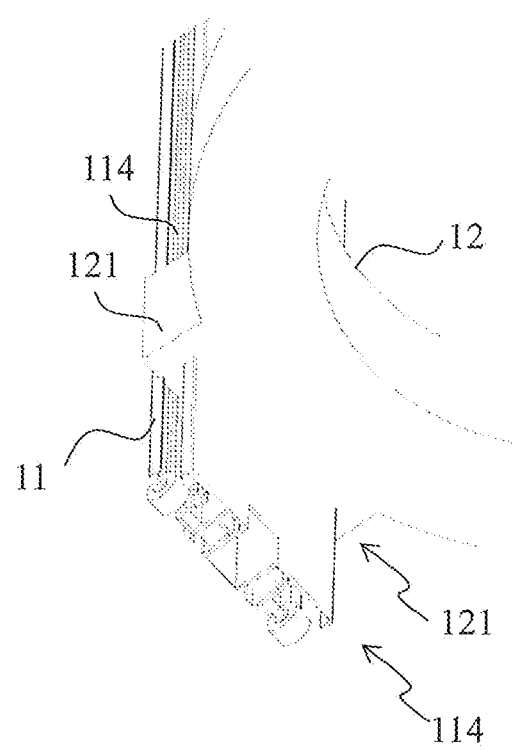

In the example according to FIG. 2a, the driving mechanism 17 of the support construction 12 discussed above comprises a motor 110 and a gearing 111 arranged to rotate a pulley 112. In the construction shown as one embodiment in FIG. 2a, while the motor 110 and the pulley 112 are located at the proximity of the bottom end of the substantially vertically extending frame part 11 there is also another pulley 112' at the proximity of the top end of the substantially vertically extending frame part 11 and around the pulleys 112, 112' goes a belt 113, or a correspondingly functioning component like a chain. This mechanism is then functionally connected to the support construction 12 to drive it along the substantially vertically extending frame part 11, such as shown as an example in FIG. 2b where grooves 114 are arranged to the substantially vertically extending frame part 11 and, to the support construction 12, projecting parts 121 which are fitted to slide along the grooves 114. In an embodiment, to minimize friction, roller type linear guide ways are used in which case the motion is rather rolling than sliding.

According to one aspect not shown in any of the FIGS., for example, the driving mechanism to drive the support construction 12 comprises a motor arranged to the support construction 12 itself.

Regardless of details of the construction of the driving mechanism 17 to drive the support construction 12, in one preferable embodiment the construction of the apparatus allows for driving the support construction 12 essentially the whole length between the top and bottom ends of the substantially vertically extending frame part 11.

According to yet another aspect and as shown is FIG. 1, the apparatus comprises a connection construction 19, 20 which connects the patient support 18 to the substantially vertically extending frame part 11.

Figure 3A:
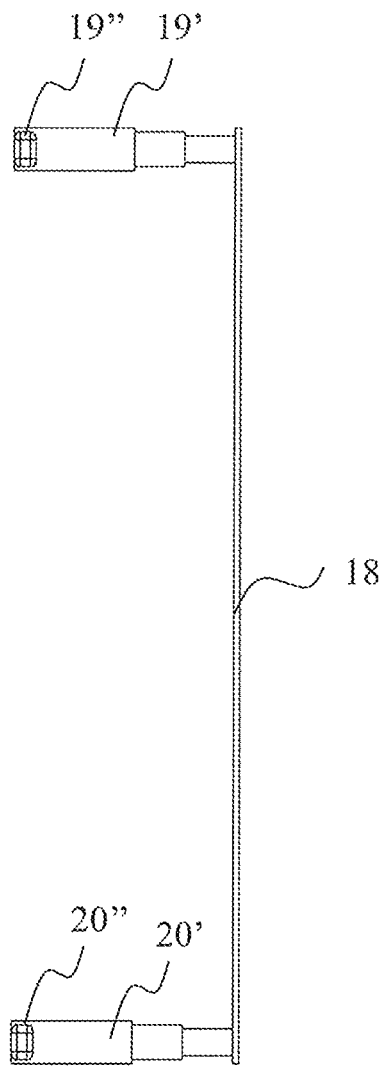
FIG. 3a shows as an example some details of a patient support construction applicable for use in an apparatus as the one shown in FIG. 1.

According to another aspect, an example of which is shown is FIG. 3a, the apparatus comprises a connection construction 19, 20 which mechanically connects the patient support 18 to the substantially vertically extending frame part 11.

The connection construction 19, 20 may comprise a patient support adjustment mechanism 19', 20' configured to enable displacing the patient support 18 closer and further away from the substantially vertically extending frame part 11.

According to another aspect, a driving mechanism 19", 20" is arranged in functional connection with the patient support adjustment mechanism 19', 20'.

According to another aspect, the patient support adjustment mechanism 19', 20' may comprise a first adjustment mechanism 19' arranged together with its driving mechanism 19" comprised in the driving mechanism 19", 20" substantially at the top end of the substantially vertically extending frame part 11, and a second adjustment mechanism 20' arranged together with its driving mechanism 20" comprised in the driving mechanism 19", 20" substantially at the bottom end of the substantially vertically extending frame part 11.

According to one aspect, for example, the patient support adjustment mechanisms 19', 20' is arranged in functional connection with the control system of the apparatus and the control system is configured to control the driving mechanism 19", 20" of the adjustment mechanism 19', 20'.

According to one aspect, for example, the control system is configured to control the connection construction 19, 20 comprising the first adjustment mechanism 19' with its driving mechanism 19", arranged substantially at the top end of the substantially vertically extending frame part 11, and the second adjustment mechanism 20' with its driving mechanism 20", arranged substantially at the bottom end of the substantially vertically extending frame part 11, to keep at the top and bottom ends of the substantially vertically extending frame part 11 an identical distance between the substantially vertically extending frame part 11 and the patient support 18 when adjusting the distance between the two.

According to another aspect, the distance between the ends of the substantially vertically extending frame part 11 and the patient support 18 can be adjusted to be different. According to one aspect, the first and second adjustment mechanisms 19', 20' are arranged to be controlled independently.

Figure 3B:
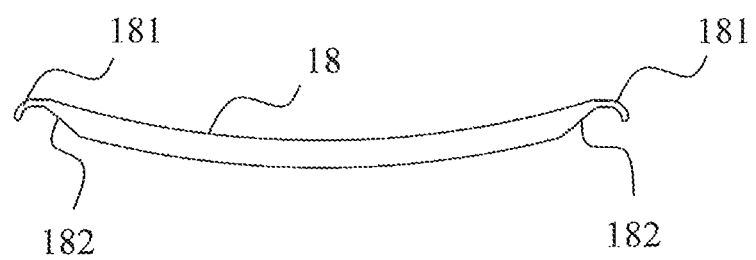
FIG. 3b shows an example of a cross section of the patient support construction applicable for use in an apparatus as the one shown in FIG. 1.

According to one aspect, as shown in FIG. 3b, considering the above-discussed first direction of the patient support construction 18, its cross section as for its prevailing part is curved so as to better support a patient against the concave surface of the patient support construction 18.

According to one other aspect, as shown in FIG. 3b, at the edges 181 of that cross section of the patient support construction 18 the shape of the cross section turns into being curved in the opposite direction.

According to one other aspect and as further shown in FIG. 3b, near the edges 181 of the above-discussed cross section of the patient support construction 18 and on the side opposite to the for its prevailing part concave surface is arranged a holding structure 182. The holding structure 182 may be e.g. an elongated handle or an attachment structure to receive a strap designed to extent on or over the concave side of the patient support construction 18, to be used to provide further support to the patient and thus to help keeping still during an imaging exposure.

Figure 4:
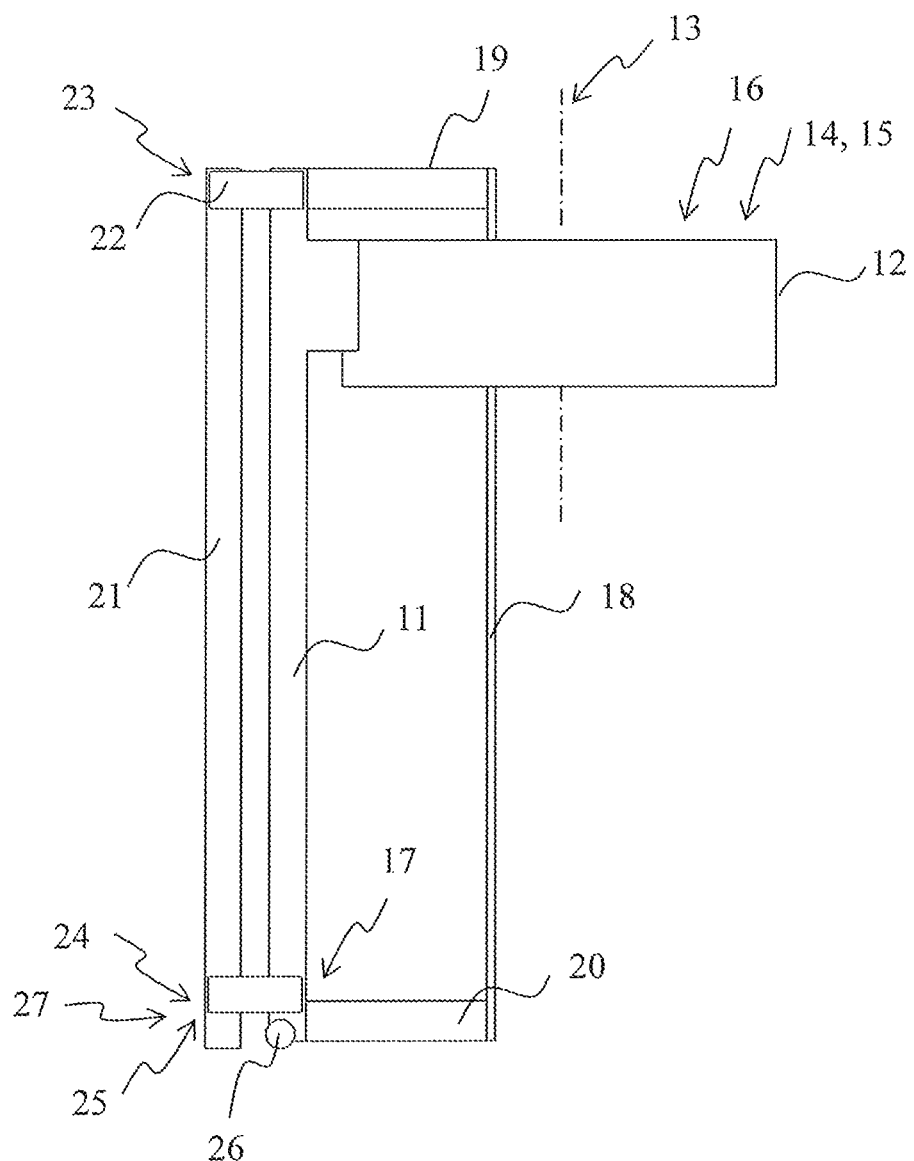
FIG. 4 is a schematic general side view showing certain components of another embodiment, as an example, of an apparatus according to the invention.

According to one aspect the apparatus further comprises, in addition to what can be referred to as a first substantially vertically extending frame part 11 discussed above, a second substantially vertically extending frame part 21 mechanically connected to the first substantially vertically extending frame part 11 of essentially the same length as the first substantially vertically extending frame part 11. FIG. 4 shows an example of such construction as a schematic general side view. According to one aspect and referring to FIG. 4, at the proximity of the top end of the first substantially vertically extending frame parts 11, 12 is arranged an articulated connection construction 22 to mechanically connect the first and second substantially vertically extending frame parts 11, 21, to allow for tilting of the first substantially vertically extending frame part 11 about a horizontal tilt axis with respect to the second substantially vertically extending frame part 21.

According to another aspect, on the side of the second substantially vertically extending frame part 21, a mounting structure 23 not directly visible in FIG. 4 is arranged in connection with the articulated connection construction 22. The mounting structure 23 may be arranged movable along or alongside the second substantially vertically extending frame part 21.

According to another aspect, for example at the proximity of the bottom end of the second substantially vertically extending frame part 21 is arranged a locking mechanism 24 configured to enable connecting and disconnecting the first and second substantially vertically extending frame parts 11, 21.

When the second substantially vertically extending frame part 21 is mounted stable and the locking mechanism 24 is not connecting the first and second substantially vertically extending frame parts 11, 21, the bottom end of the first substantially vertically extending frame part 11 is free to move horizontally while the articulated connection 22 between the frame parts 11, 21 allows for turning of the first substantially vertically extending frame part 11 about the horizontal tilt axis at the proximity of the top end of the first substantially vertically extending frame part 11, while the movably arranged mounting structure 23 allows for descending and ascending of the top end of the first substantially vertically extending frame part 11.

Figure 5:
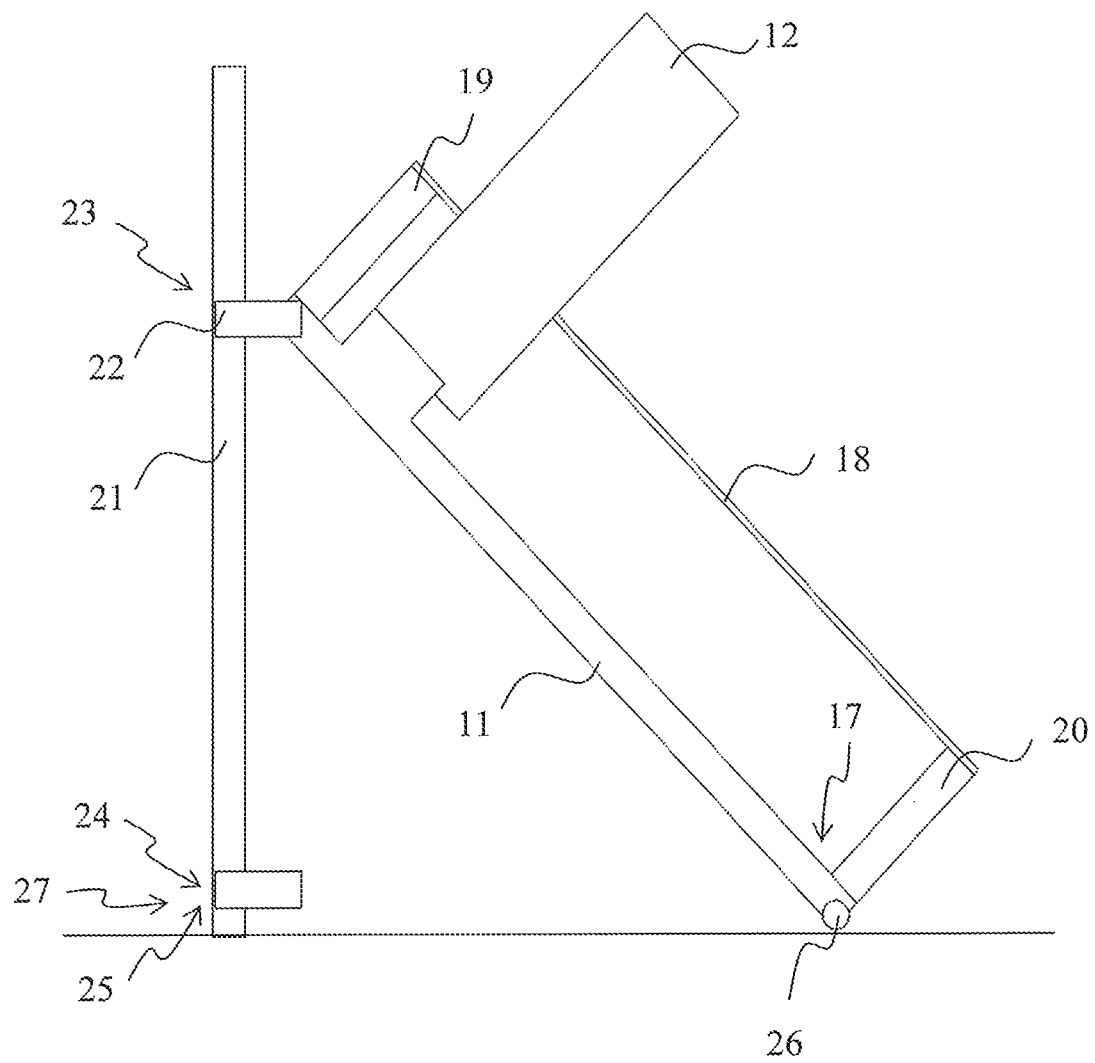
FIG. 5 is a schematic general side view of the apparatus of FIG. 4 showing certain components of the construction as driven at an inclined position.

FIG. 5 shows the apparatus according to FIG. 4 at a stage where the top end of the first substantially vertically extending frame part 11 has moved downwards and the bottom end of the first substantially vertically extending frame part 11 has moved horizontally on a surface. The apparatus may be configured to allow for descending of the top end of the first substantially vertically extending frame part 11 all the way to the proximity of the bottom end of the second substantially vertically extending frame part 21.

According to yet another aspect, not directly visible in FIGS. 4 and 5, in functional connection with the second substantially vertically extending frame part 21 is arranged a driving mechanism 27 to drive the mounting structure 23 along or alongside the second substantially vertically extending frame part 21. When being in mechanical connection with the first substantially vertically extending frame part 11, at the proximity of the top end of it, the driving mechanism 27 can move the top end of the first substantially vertically extending frame part 11.

The driving mechanism 27 to drive the mounting structure 23 may be a construction similar to the driving mechanism 17 driving the support construction 12 of the imaging means 14, 15.

According to one aspect, the driving mechanism 27 to drive the mounting structure 23 comprises a chain drive.

According to yet another aspect, the locking mechanism 24 comprises a displacement mechanism 25, which is not directly visible in FIGS. 4 and 5, to move the bottom end of the first substantially vertically extending frame part 11 a distance away from the second substantially vertically extending frame part 21 when the locking mechanism 24 disconnects the first and second substantially vertically extending frame parts 11, 21.

According to one aspect not shown in detail in the FIGS., for example, the locking mechanism 24 comprises a motor driven arrangement with mating components on the side of a motorized structure and the first substantially vertically extending frame part 11, respectively.

The locking mechanism 24 may further comprise a guiding construction configured to guide the bottom end of the first substantially vertically extending frame part 11 straight on the locking mechanism 24 when the bottom end of the first substantially vertically extending frame part 11 is moving towards the locking mechanism 24.

According to yet another aspect and, as shown as an example in FIGS. 4 and 5, the first substantially vertically extending frame part 11 comprises at the proximity of its bottom end at least one wheel or roller 26.

According to another aspect, instead of the wheel or roller, a structure designed to slide on a surface may be arranged at the bottom end of the first substantially vertically extending frame part 11.

Figure 6:
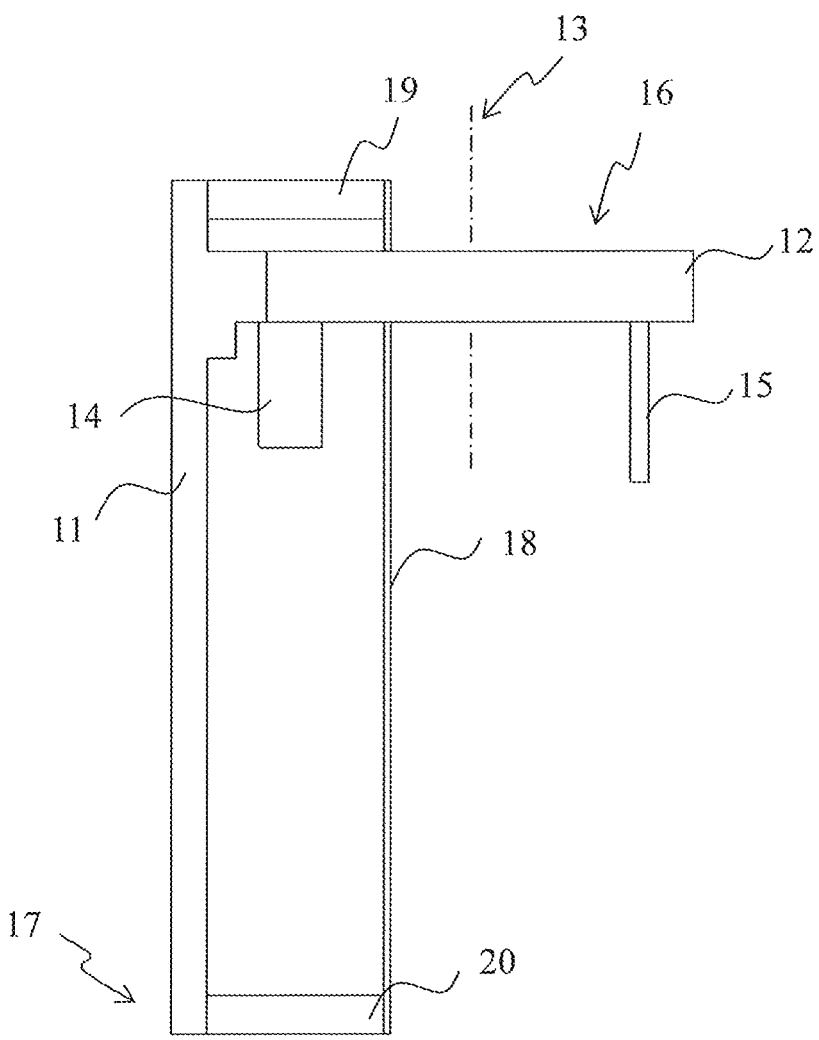
FIG. 6 is a schematic general side view showing certain components of yet another embodiment, as an example, of an apparatus according to the invention.

According to one aspect, for example and as shown in FIG. 6, support construction 12 for the imaging means 15, 16 in a form of a gantry basically does not completely encircle the imaging means 14, 15 but functions primarily or solely as a support structure for holding the imaging means 14, 15, and structures arranged to the gantry to drive the imaging means 14, 15 about an axis. This kind of solution enables realizing the gantry as less heavy and as providing better access to the volume between the imaging means 14, 15, both physically and considering an area from where one may have a clear line of sight at that volume.

Figure 7:
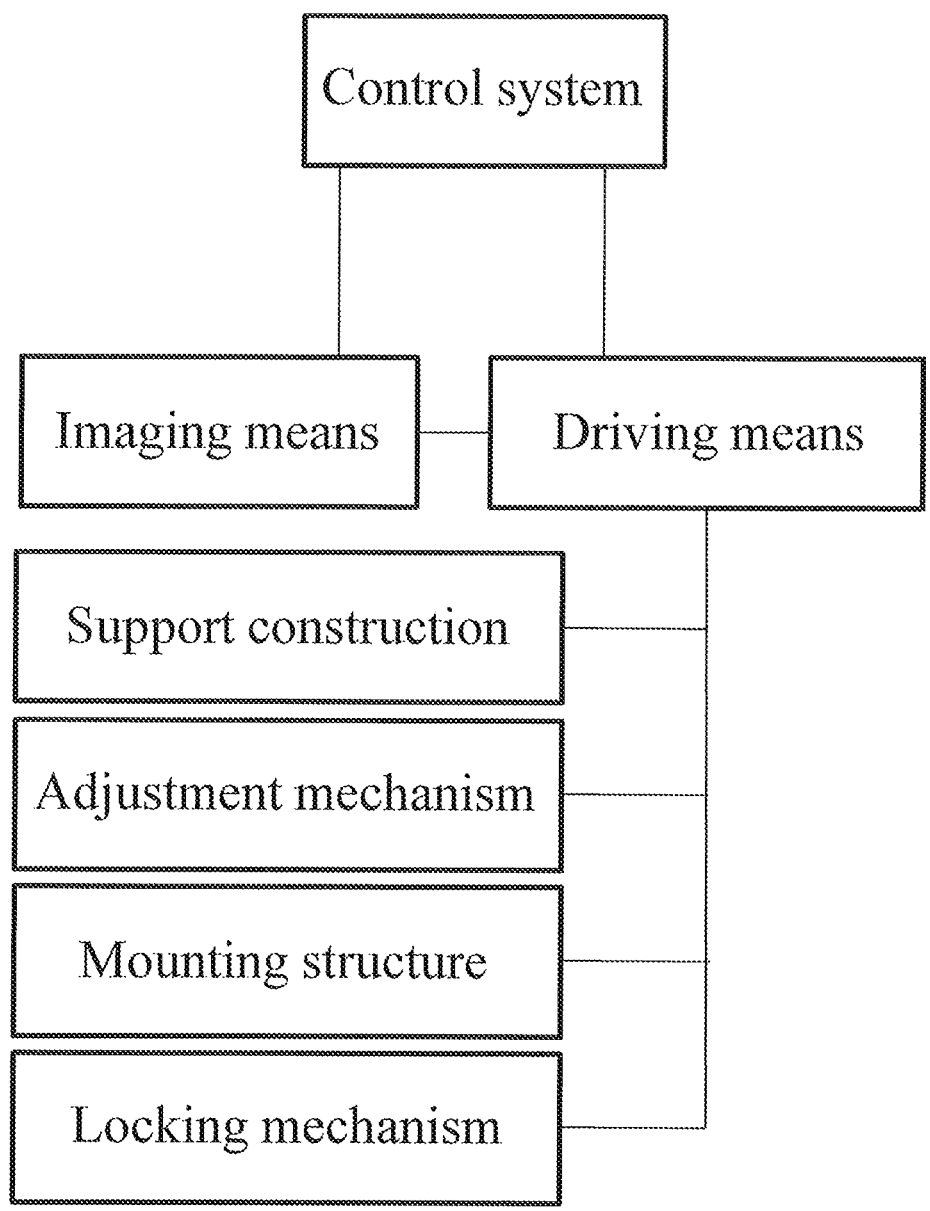
FIG. 7 is a block diagram showing an example of components which a control system of an apparatus according to the invention may be configured to control.

FIG. 7 shows as a block diagram an example of components of a control system applicable for use in an apparatus according to this disclosure. In various embodiments, not all those features are necessarily present in a control system of the apparatus. The control system according to FIG. 7 is configured to enable controlling, first of all, operation of the x-ray source and the image detector. Components controlling operation of the x-ray source and the image detector can include components physically arranged to the x-ray source and the image detector and/or elsewhere in the apparatus. The control system of FIG. 7 further controls various driving means of the apparatus, such as those moving the imaging means supported by the support construction, the support construction itself and the adjustment mechanism of the patient support. In case of an embodiment including both the first and second substantially vertically extending frame parts, the control system may also control e.g. driving of the mounting structure as discussed above. Further, in case of the apparatus comprising a motorized locking mechanism to connect and disconnect the first and second substantially vertically extending frame parts, the control system may also control driving means of the locking mechanism. Overall, the control system may be arranged to control all the above-discussed operations or any portion thereof.

The invention claimed is:
1. A dental or medical CT imaging apparatus, comprising:
a first substantially vertically extending frame part comprising a top end and a bottom end;
a support construction extending essentially horizontally from the first substantially vertically extending frame part;
an X-ray source and an image detector mounted to the support construction which together form an X-ray imaging means;
a first driving mechanism arranged to move the imaging means, about an axis;
a second driving mechanism arranged to move the support construction in a direction substantially parallel with a direction in which the substantially vertically extending frame part extends;
a patient support;
a control system;
characterized in that the patient support is a structure mechanically connected to the first substantially vertically extending frame part and extending substantially in parallel with said first substantially vertically extending frame part and is essentially of the same length as said first substantially vertically extending frame part.

2. An apparatus according to claim 1, characterized in that the length of the first substantially vertically extending frame part is between 220 cm and 260 cm, or that the length of the substantially vertically extending frame part is of the order of 240 cm.

3. An apparatus according to claim 1, characterized in that the length of the patient support is 80-90% of the length of the first substantially vertically extending frame part.

4. An apparatus according to claim 1, characterized in that the patient support has a longer dimension in a first direction and a shorter dimension in a second direction orthogonal to the first direction.

5. An apparatus according to claim 1, characterized in that the patient support is at least in said first direction at least for its prevailing part radiolucent wherein the patient support optionally comprises at least at either of its ends in said first direction a section which is not radiolucent, and wherein optionally the length of the radiolucent part of the patient support in said first direction is 80-90% of the length of the first substantially vertically extending frame part.

6. An apparatus according to claim 5, characterized in that the radiolucent part of the patient support is of essentially the same length as the length of the first substantially vertically extending frame part.

7. A dental or medical CT imaging apparatus, comprising:
a first substantially vertically extending frame part comprising a top end and a bottom end;
a support construction extending essentially horizontally from the first substantially vertically extending frame part;
an X-ray source and an image detector mounted to the support construction which together form an X-ray imaging means;
a first driving mechanism arranged to move the imaging means, about an axis;
a second driving mechanism arranged to move the support construction in a direction substantially parallel with a direction in which the substantially vertically extending frame part extends;
a patient support;
a control system;
characterized in that the patient support is a structure mechanically connected to the first substantially vertically extending frame part and extending substantially in parallel with said first substantially vertically extending frame part and is essentially of the same length as said first substantially vertically extending frame part, and
characterized in that the apparatus comprises a first connection construction, which mechanically connects the patient support to the first substantially vertically extending frame part, said first connection construction, comprising a patient support adjustment mechanism, configured to enable displacing the patient support closer and further away from the first substantially vertically extending frame part.

8. An apparatus according to claim 7, characterized in that the apparatus comprises a third driving mechanism, arranged in functional connection with said patient support adjustment mechanism.

9. An apparatus according to claim 8, characterized in that the patient support adjustment mechanism, comprises a first adjustment mechanism which is arranged, together with its driving mechanism comprised in said third driving mechanism, substantially at the top end of the first substantially vertically extending frame part and a second adjustment mechanism which is arranged, together with its driving mechanism comprised in said third driving mechanism, substantially at the bottom end of the first substantially vertically extending frame part.

10. An apparatus according to claim 8, characterized in that the control system is configured to control the third driving mechanism, arranged in functional connection with said patient support adjustment mechanism.

11. An apparatus according to claim 10, characterized in that the control system is configured to control the first connection construction, comprising the first adjustment mechanism with its driving mechanism, arranged substantially at the top end of the first substantially vertically extending frame part, and the second adjustment mechanism with its driving mechanism, arranged substantially at the bottom end of the first substantially vertically extending frame part, to keep at the top and bottom ends of the first substantially vertically extending frame part an identical distance between the first substantially vertically extending frame part and the patient support when adjusting the distance between the two.

12. An apparatus according to claim 1, characterized in that the second driving mechanism is arranged to move the support construction along or alongside the first substantially vertically extending frame part.

13. A dental or medical CT imaging apparatus, comprising:
a first substantially vertically extending frame part comprising a top end and a bottom end;
a support construction extending essentially horizontally from the first substantially vertically extending frame part;

an X-ray source and an image detector mounted to the support construction which together form an X-ray imaging means;

a first driving mechanism arranged to move the imaging means, about an axis;

a second driving mechanism arranged to move the support construction in a direction substantially parallel with a direction in which the substantially vertically extending frame part extends;

a patient support;

a control system;

characterized in that the patient support is a structure mechanically connected to the first substantially vertically extending frame part and extending substantially in parallel with said first substantially vertically extending frame part and is essentially of the same length as said first substantially vertically extending frame part, and characterized in that the apparatus comprises a second substantially vertically extending frame part as mechanically connected to the first substantially vertically extending frame part, said second substantially vertically extending frame part being of essentially the same length as the first substantially vertically extending frame part.

14. An apparatus according to claim 13, characterized in that at the proximity of the top end of the first substantially vertically extending frame parts, is arranged an articulated connection construction to mechanically connect the first and second substantially vertically extending frame parts, and to allow for tilting of the first substantially vertically extending frame part about a horizontal tilt axis with respect to the second substantially vertically extending frame part.

15. An apparatus according to claim 14, characterized in that in connection with said articulated connection construction, on the side of the second substantially vertically extending frame part, is arranged a mounting structure.

16. An apparatus according to claim 15, characterized in that the mounting structure is arranged movable along or alongside the second substantially vertically extending frame part.

17. An apparatus according to claim 15, characterized in that in functional connection with the second substantially vertically extending frame part is arranged a fourth driving mechanism to drive the mounting structure along or alongside the second substantially vertically extending frame part.

18. An apparatus according to claim 13, characterized in that at the proximity of the bottom end of the second substantially vertically extending frame part is arranged a locking mechanism configured to enable connecting and disconnecting the first and second substantially vertically extending frame parts.

19. An apparatus according to claim 18, characterized in that the locking mechanism comprises a displacement mechanism configured to push the bottom end of the first substantially vertically extending frame part a distance away from the second substantially vertically extending frame part when the locking mechanism disconnects the first and second substantially vertically extending frame parts.

20. An apparatus according to claim 1, characterized in that the first substantially vertically extending frame part comprises at the proximity of its bottom end at least one wheel or roller, or a structure designed to slide on a surface.

* * * * *